(12) United States Patent
Gao et al.

(10) Patent No.: US 11,065,338 B2
(45) Date of Patent: Jul. 20, 2021

(54) POLYSACCHARIDE THERAPEUTIC CONJUGATES

(71) Applicant: CASE WESTERN RESERVE UNIVERSITY, Cleveland, OH (US)

(72) Inventors: Songqi Gao, Beachwood, OH (US); Krzysztof Palczewski, Bay Village, OH (US); Zheng-Rong Lu, Beachwood, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 16/299,841

(22) Filed: Mar. 12, 2019

(65) Prior Publication Data

US 2019/0216937 A1 Jul. 18, 2019

Related U.S. Application Data

(63) Continuation of application No. 14/361,163, filed as application No. PCT/US2012/066847 on Nov. 28, 2012, now Pat. No. 10,226,536.

(60) Provisional application No. 61/563,940, filed on Nov. 28, 2011.

(51) Int. Cl.
| | |
|---|---|
| *A61K 47/61* | (2017.01) |
| *A61K 31/07* | (2006.01) |
| *A61K 31/11* | (2006.01) |
| *A61K 31/722* | (2006.01) |

(52) U.S. Cl.
CPC .............. *A61K 47/61* (2017.08); *A61K 31/07* (2013.01); *A61K 31/11* (2013.01); *A61K 31/722* (2013.01)

(58) Field of Classification Search
CPC ........ A61K 47/61; A61K 31/11; A61K 31/07; A61K 31/722
USPC ...................................................... 536/123.1
See application file for complete search history.

(56) References Cited

U.S. PATENT DOCUMENTS

| | | | |
|---|---|---|---|
| 5,622,718 | A | 4/1997 | Al-Shamkhani et al. |
| 5,700,848 | A | 12/1997 | Soon-Shiong et al. |
| 6,472,506 | B1 | 10/2002 | Moreau et al. |
| 2003/0161791 | A1 | 8/2003 | Bentley et al. |
| 2004/0028745 | A1 | 2/2004 | Bouhadir et al. |
| 2005/0271705 | A1 | 12/2005 | Hughes et al. |
| 2008/0221208 | A1 | 9/2008 | Palczewski et al. |
| 2010/0035986 | A1 | 2/2010 | Maeda et al. |
| 2011/0288170 | A1 | 11/2011 | Palczewski et al. |

FOREIGN PATENT DOCUMENTS

| | | |
|---|---|---|
| CN | 101745119 A | 6/2010 |
| EP | 3223016 A1 | 9/2017 |
| GB | 1334980 A | 10/1973 |

OTHER PUBLICATIONS

Liu et al. Polysaccharides-based nanoparticles as drug delivery systems. Advanced Drug Delivery Reviews 60 (2008) 1650-1662. (Year: 2008).*
Zheng Han et al.: "An EDB fibronectin specific contrast agent for molecular imaging of cancer metastasis" 23rd Annual Meeting & Exhibition May 30-Jun. 2015, Proc. Intl. Soc. Mag. Reson. Med., vol. 23, Jun. 3, 2015, XP009502183, Retrieved from the Internet: URL: http://dev.ismrm.org/2015/1910.html [retrieved on Dec. 6, 2015].
Zheng Han, et al.: "EDB Fribronectin Specific Peptide for Prostate Cancer Targeting", Bioconjugate Chemistry, vol. 26, No. 5, May 20, 2015, pp. 830-838, XP055432466, ISSN: 1043-1802, DOI: 10.1021/acs.bioconjchem.5b00178.
Wang, Wei, et al.: "Screening and identifying of homing peptides to bladder cancer BIU-87 cells in Chinese", CHIN. J. Cancer Biother., vol. 20, No. 5, Oct. 2013, pp. 515-521, XP002776454, abstract; figures 2-3.
Yujin Sun, et al.: "MRI of Breast Tumor Initiating Cells Using the Extra Comain-B of Fibronectin Targeting Nanoparticles", Theranostics, vol. 4, No. 8, Jan. 1, 2014, pp. 845-857, XP055432454, au issn: 1838-7460, doi: 10.7150/thno.8343.
Applicant: Case Western Reserve University; International Application No. 19211484.1; Filing Date: Nov. 26, 2019; European Search Report; Examiner: Philippe Hoff; dated May 27, 2020; 11 pgs.

* cited by examiner

*Primary Examiner* — Yih-Horng Shiao
(74) *Attorney, Agent, or Firm* — Tarolli, Sundheim, Covell & Tummino LLP

(57) ABSTRACT

A composition includes a polysaccharide at least one retinoid linked to at least one monosaccharide subunit of the polysaccharide with a covalent linkage. The linkage being degradable by hydrolysis during digestion of the composition to provide controlled, delayed, and/or sustained delivery of the at least one retinoid upon enteral administration of the composition to a subject.

14 Claims, 8 Drawing Sheets

Alginic Acid

GGGG (homopolymeric guluronic acid)

MMM (homopolymeric mannuronic acid)

MGM (heteropolymeric region)

MW, 3-10 KDa

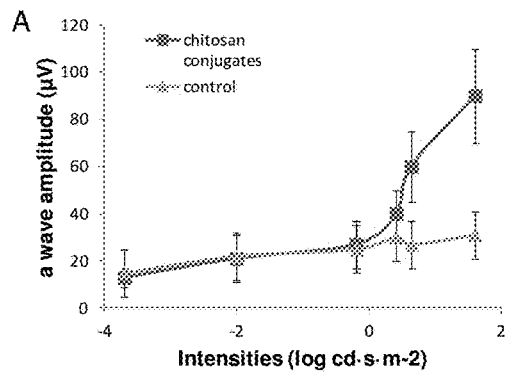
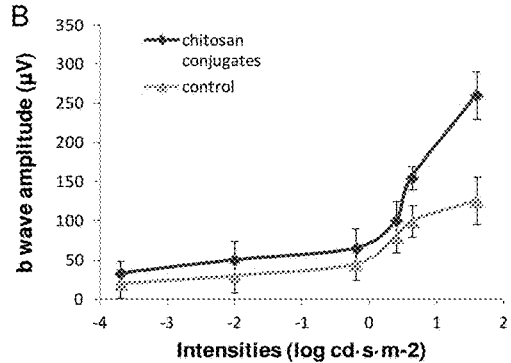
Fig. 7A    Fig. 7B
Dose 0.012 mg/mouse (equivalent to 9-cis retinol) for 6 oral gavages in 2 weeks Lrat -/- mice housed in dark room
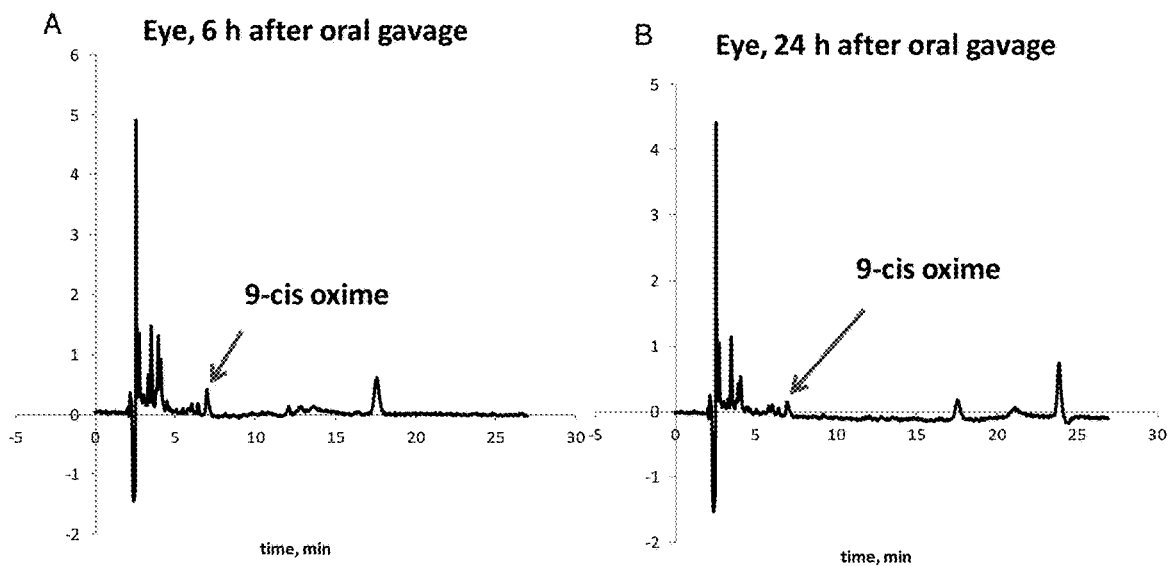
9-cis oxime are detected in eyes after oral gavage
Fig. 8A    Fig. 8B

LRAT control

**LRAT treated
(cone are much better preserved)**

ary metabolites and retinoid analogues have shown effectiveness in many clinical settings that include skin diseases and cancer, and in animal models of human conditions affecting vision. Retinoid therapies have demonstrated clinical efficacy as treatments for many debilitating diseases.

POLYSACCHARIDE THERAPEUTIC CONJUGATES

RELATED APPLICATION

This application claims priority from U.S. Provisional Application No. 61/653,940, filed Nov. 28, 2011, the subject matter of which is incorporated herein by reference in its entirety.

BACKGROUND

Through its various metabolites, vitamin A, retinol, controls essential physiological functions. Both naturally occurring metabolites and retinoid analogues have shown effectiveness in many clinical settings that include skin diseases and cancer, and in animal models of human conditions affecting vision. Retinoid therapies have demonstrated clinical efficacy as treatments for many debilitating diseases.

Typically, retinoids are complexed with soluble proteins that protect them. These reactive compounds are bound by a number of retinoid-binding proteins, and are rarely freely solubilized from membranes. Protection of retinoids also stems from their ability to cluster when esterified by long-chain fatty acids, and undergo storage in lipid-like droplets in the liver or as retinosomes in the eye. Evidence that esterification of retinol and retinol-based drugs within target tissues provides one of the most efficient means to improve the absorption and to reduce the toxicity associated with pharmacological doses of retinoids. Currently, there are few treatments for retinoid deficiency. Thus, there is a need for compositions and methods of restoring or stabilizing photoreceptor function and ameliorating the effects of deficient levels of endogenous retinoids.

SUMMARY

Embodiments described herein relate to polysaccharide therapeutic conjugate compositions that provide controlled release, delayed release, and/or sustained delivery of a therapeutic agent upon enteral administration of the composition to a subject. The compositions include a polysaccharide and at least one therapeutic agent that is linked to at least one monosaccharide subunit of the polysaccharide with a covalent linkage. The linkage is degradable by hydrolysis during digestion of the composition to provide controlled release, delayed release, and/or sustained delivery of the therapeutic agent upon enteral administration of the composition to the subject. In one example, the therapeutic agent can include a retinoid, and the retinoid is released or delivered at a rate effective to provide sustained treatment of an ocular disorder, such as a retinal disease associated with inadequate production of 11-cis-retinal.

Other embodiments described herein relate to a method for preparing a polysaccharide therapeutic conjugate composition. The method includes reacting the at least one retinoid with a chlorinating agent to provide at least one retinoid having a primary chloride functional group. The at least one retinoid having a primary chloride functional group is then reacted with a monosaccharide subunit of the polysaccharide having a carboxylate functional group in the presence of a phase transfer catalyst. The phase transfer catalyst catalyzes the formation of a hydrolysable carboxylic ester covalent linkage between the monosaccharide subunit and the at least one retinoid.

Further embodiments described herein relate to a method for treating a retinal disease in a subject. The method includes administering to the subject a therapeutically effective amount of a polysaccharide therapeutic conjugate composition. The composition includes a polysaccharide and at least one retinoid that is linked to at least one monosaccharide subunit of the polysaccharide with a covalent linkage. The linkage is degradable by hydrolysis during digestion of the composition to provide controlled release, delayed release, and/or sustained delivery of the retinoid upon enteral administration of the composition to the subject. In one example, the retinoid is released or delivered at a rate effective to provide sustained treatment of an ocular disorder, such as a retinal disease associated with inadequate production of 11-cis-retinal.

BRIEF DESCRIPTION OF THE DRAWINGS

FIGS. 7(A-B) illustrate plots showing ERG response in 5-week-old Lrat$^{-/-}$ mice after oral gavage of chitosan-9-cis-retinol conjugates.

FIGS. 8(A-B) illustrate plots showing in 9-cis-oxime levels in eyes of 5-week-old Lrat$^{-/-}$ mice after oral gavage of chitosan-9-cis-retinol conjugates.

DETAILED DESCRIPTION

Figure 1:
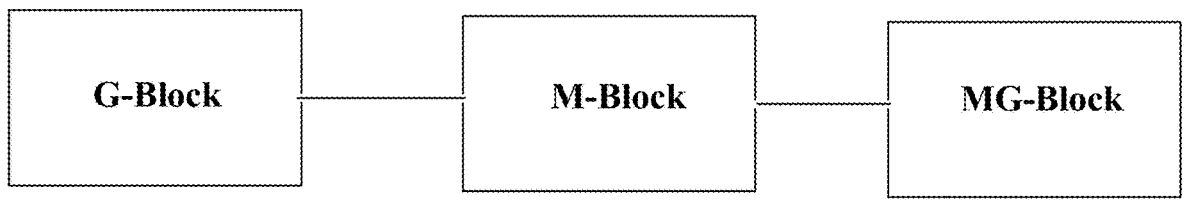
FIG. 1 illustrates a generalized structure of an alginic acid block copolymer. The block copolymer includes a homopolymeric block of guluronic acid (G-block), a homopolymeric block of mannuronic acid (M-block) and a block of alternating M and G-residues (MG-block). Also illustrated are generalized formulas of a G-block (GGGG), a M-block (MMM) and a MG-block (MGM).
Figure 1:
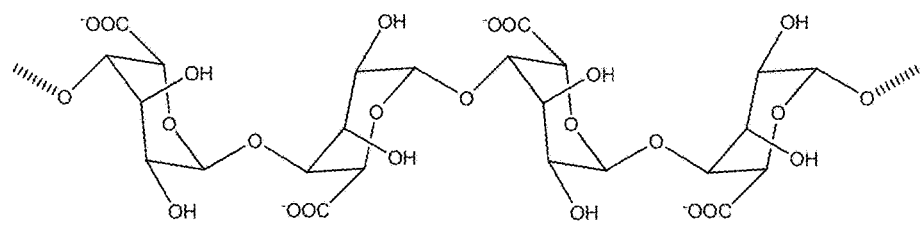
Figure 1:
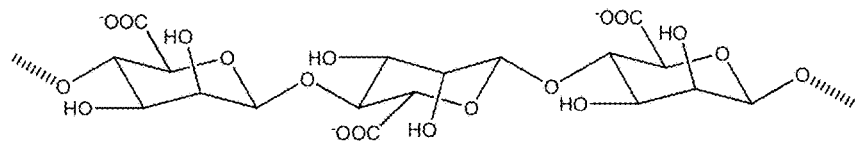
Figure 1:
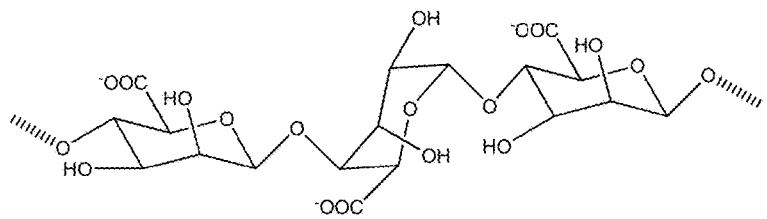

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

The terms "therapeutic agent," "drug" and "active agent" are used interchangeably herein to refer to a chemical material or compound which, when administered to an organism (human or animal, generally human) induces a desired pharmacologic effect.

The term "polysaccharide" is intended to include naturally occurring polysaccharides as well as polysaccharides that are obtained via chemical synthesis or genetic engineering. The term is used to include disaccharides, oligosaccharides and longer saccharide polymers, wherein the individual monomeric saccharide units may be naturally occurring or modified. Modified saccharides include those wherein one or more of the hydroxyl groups are replaced with halogen, aliphatic groups, or are functionalized as ethers, amines, phosphates, or the like. Intersugar linkages within the polysaccharide structure may be $\alpha$-1,2, $\alpha$-1,3, $\alpha$-1,4, $\alpha$-1,6, $\beta$-1,2, $\beta$-1,3, $\beta$-1,4, $\beta$-1,6 linkages, or the like.

By the terms "effective amount" or "pharmaceutically effective amount" of an agent as provided herein are meant a non-toxic but sufficient amount of the agent to provide the desired therapeutic effect. As will be pointed out below, the exact amount required will vary from subject to subject, depending on age, general condition of the subject, the severity of the condition being treated, and the particular active agent administered, and the like. An appropriate "effective" amount in any individual case may be determined by one of ordinary skill in the art by reference to the pertinent texts and literature and/or using routine experimentation.

By "pharmaceutically acceptable" is meant a carrier comprised of a material that is not biologically or otherwise undesirable.

The term "transmembrane" refers to the passage of a substance into or through a body membrane, e.g., a mucosal membrane such as the gastrointestinal, sublingual, buccal, nasal, pulmonary, vaginal, corneal, or ocular membranes, so as to achieve a desired therapeutic or prophylactic effect.

The terms "absorption" and "transmembrane absorption" as used herein refer to the rate and extent to which a substance passes through a body membrane.

The term "controlled release" is intended to refer to any therapeutic agent-containing formulation in which the manner and profile of drug release from the formulation are controlled. The term "controlled release" refers to immediate as well as nonimmediate release formulations, with nonimmediate release formulations including but not limited to sustained release and delayed release formulations.

The term "delayed release" is used in its conventional sense to refer to a delay in release of a composition from a dosage form following oral administration, such that the majority of the composition is released in the lower gastrointestinal (GI) tract. After the dosage form reaches the intended release site, there may or may not be a further mechanism controlling the release of the composition from the dosage form. "Delayed release" may thus be an immediate release of all the contents of a drug dosage form, or it may involve controlled release in a sustained manner or in a staged or pulsatile fashion (e.g., when a multi-component device is utilized), wherein the term "sustained" means that release occurs during an extended time period, and the terms "staged" and "pulsatile" mean that release occurs in two or more spaced apart pulses.

The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds described herein can be delivered in prodrug form. Prodrugs can be prepared by modifying functional groups present in the compound in such a way that the modifications are cleaved, either in routine manipulation or in vivo, to the parent compound. Prodrugs include compounds described herein wherein a hydroxy, amino, sulfhydryl, carboxy, or carbonyl group is bonded to any group that may be cleaved in vivo to form a free hydroxyl, free amino, free sulftydryl, free carboxy or free carbonyl group, respectively.

The term "treating" refers to inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

Embodiments described herein relate to polysaccharide therapeutic conjugate compositions that provide controlled release, delayed release, and/or sustained delivery of a therapeutic agent upon enteral administration of the composition to a subject. The release and/or delivery of the therapeutic agent is controlled, delayed, and/or sustained in nature, such that the release and/or delivery of the therapeutic agent from the dosage form is controlled, delayed, and/or sustained after oral administration, and, for example, such that it occurs in the lower GI tract. That is, controlled, delayed, and/or sustained delivery or release of the therapeutic from the composition or dosage form may occur in a sustained fashion over an extended period of time (e.g., hours, days, or weeks), or in a staged or pulsatile fashion.

The polysaccharide therapeutic conjugates compositions include therapeutic agents that are covalently linked to a biodegradable polysaccharide with a degradable or cleavable linker. The degradable or cleavable linker provides the polysaccharide therapeutic conjugate compositions described herein with increased thermodynamic stability and absorption time of the therapeutic agent upon enteral administration compared to administration of the therapeutic agent alone. The polysaccharide therapeutic conjugate compositions can thus be used as highly dense therapeutic agents for the treatment of diseases or disorders where controlled release, delayed release, and/or sustained delivery of a therapeutic agent is desired.

In some embodiments, the polysaccharide therapeutic conjugate composition includes a polysaccharide and at least one retinoid. The at least one retinoid can be linked to at least one monosaccharide subunit of the polysaccharide with a covalent linkage. The covalent linkage can be degradable by hydrolysis or hydrolyzable during digestion of the composition to provide controlled, delayed, and/or sustained delivery of the retinoid upon enteral administration of the composition to a subject. The controlled, delayed, and/or sustained release can allow therapeutic levels of retinoid to be maintained in the subject for house, days, and/or weeks without the need for constant and/or continuous administration of the retinoid.

In some embodiments, the covalent linkage is a hydrolyzable covalent linkage, e.g., an acid-labile linkage, that is cleavable under physiological conditions of the lower gastrointestinal (GI) tract, e.g., intestines, to provide controlled, delayed, and/or sustained delivery or release of the retinoid to treat an ocular disorder, such as a retinal disease associated with inadequate production of 11-cis-retinal.

An example of a hydrolysable covalent linkage that slowly degrades or hydrolyzes during digestion of the composition includes a hydrolysable acrylate, ester, ether, thioether, disulfide, amide, imide secondary amine, direct carbon (C—C), carboxylic ester, sulfate ester, sulfonate ester, phosphate ester, urethane, and/or carbonate covalent linkage. In certain embodiments, the hydrolysable covalent linkage can include a hydrolysable carboxylic ester linkage. For example, carboxylic ester linkages refer to a structure of either:

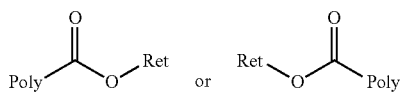

wherein Poly and Ret denote a monosaccharide subunit of a polysaccharide and a retinoid respectively.

The retinoid and the polysaccharide can be covalently linked directly or with a linker or spacer. The spacer can include alkyl or aryl chains, such as an alkyl group, an alkenyl group, an alkynyl group, an aryl group. In some embodiments, the alkyl group is a $C_1$-$C_{15}$, $C_1$-$C_{10}$, $C_1$-$C_5$, or a $C_1$-$C_3$ alkyl, alkenyl, alkynyl, or aryl group. In some embodiments, a spacer can include two or more functional groups allowing for hydrolysable covalent bonds to a monosaccharide subunit of a polysaccharide and to the retinoid.

In this case, hydrolysis of the bond between the retinoid and the spacer will release the therapeutic, while, hydrolysis of the bond between the spacer and the polysaccharide will provide a prodrug which will not be active until the linkage or bond between the retinoid and linking compound is hydrolyzed. Providing a prodrug in this manner may be advantageous in certain controlled, delayed, and/or sustained release applications.

The polysaccharide of the polysaccharide therapeutic conjugate composition can include any polysaccharide having at least one monosaccharide subunit capable of forming a covalent linkage with a retinoid as described herein. In some embodiments, the polysaccharide is a water-soluble polymer that is capable of forming hydrolysable covalent linkages with multiple molecules of one or more retinoids per molecule of polysaccharide thereby forming polysaccharide-retinoid conjugates.

In some embodiments, the monosaccharide subunit capable of forming a covalent linkage with a retinoid is a monosaccharide compound containing uronic acids or uronic acid derivatives. A uronic acid has a carboxylic group (—COOH) on the terminal carbon that is not part of the sugar ring structure subunit making the carboxylic group available to form a covalent linkage with a retinoid as described herein. Examples of uronic acids and uronic acid derivatives include galacturonic acid, glucuronic acid, mannuronic acid, their lactones, their esters, and their amides, which can be produced by known methods.

In some embodiments, the polysaccharide can include polymers comprised of uronic acid monosaccharide subunits. In some embodiments, the polysaccharide can include alginic acids (also known as algin or alginate). Alginic acids occur as linear copolymers of (1-4)-linked β-D-mannuronate (M) and its C-5 epimer α-L-guluronate (G) residues, respectively, covalently linked together in different sequences or blocks referred to as "block copolymers". As illustrated in FIG. 1, the monomers can appear in homopolymeric blocks of consecutive G-residues (G-blocks), consecutive M-residues (M-blocks) or alternating M and G-residues (MG-blocks). For example, a block polymer of aginic acid or another polysaccharide can be referred to as a "diblock copolymer" if it contains two different homopolymeric (G or M) or alternating (MG) blocks. Triblocks, tetrablocks, multiblocks, etc. can also be made.

Alginic acid is a natural acidic polysaccharide extracted from so called brown algae (Phaecophyceae) with a high molecular weight varying between about 30,000 and 200,000 or higher, and containing chains formed by D-mannuronic acid and L-guluronic acid. The degree of polymerization varies according to the type of alga used for extraction, the season in which the algae were gathered and the place of origin of the algae, as well as the age of the plant itself. The main species of brown algae used to obtain alginic acid are, for example, *Macrocystis pyrifera*, *Laminaria cloustoni*, *Laminaria hyperborea*, *Laminaria flexicaulis*, *Laminaria digitata*, *Laminaria japonica*, *Ascophyllum nodosum*, *Lessonia flavicans*, *Durvillea antartica*, *Ecklonia maxima* and *Fucus serratus*. It is also produced by two bacterial genera *Pseudomonas* and *Azotobacter*.

The alginic acid to be used as a starting material may be any commercially available alginic acid. For the case in which polyguluronic acids are the main target products, an alginic acid rich in G blocks is preferred. Alginic acids extracted from the seaweeds *Laminaria hyperborea* and *Lessonia flavicans* are particularly rich in G-blocks. For the case in which polymannuronic acids are the main target products, an alginic acid rich in M blocks is preferred. Alginic acids extracted from the seaweeds *Laminaria japonica* and *Durvillea antartica* are particularly rich in M-blocks. For the case in which random polymers containing guluronic acid and mannuronic acid are the main target products, an alginic acid rich in MG blocks is preferred. Alginic acids extracted from the seaweed *Ecklonia maxima* are particularly rich in MG-blocks. Alternatively, synthetically prepared alginates having a selected M and G unit proportion and distribution prepared by synthetic routes, such as those analogous to methods known in the art, can be used.

Figure 2:
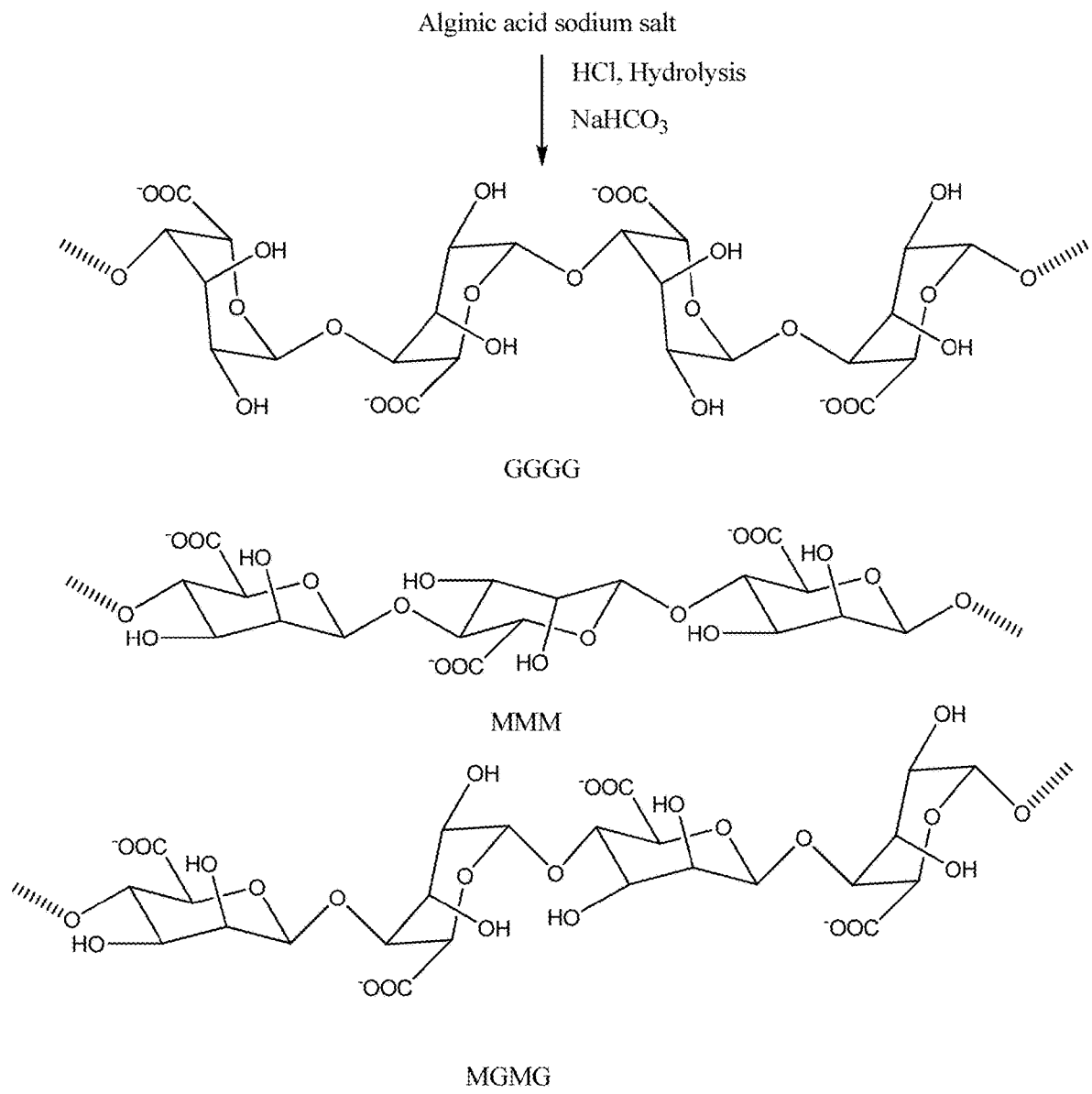
FIG. 2 is a schematic illustration showing a hydrolysis reaction of alginic acid sodium salt.

In some embodiments, it may be advantageous to create smaller block units of alginate prior to synthesizing retinoid-alginate conjugates. Therefore, the alginate material may be treated to provide a material of lower molecular weight, particularly at or below the renal threshold for clearance by humans. In some embodiments, the alginate or any other polysaccharide is reduced to a molecular weight of about 1000 to about 80,000 daltons, for example, about 1000 to about 60,000 daltons. The reduction in molecular weight can be effected by hydrolysis under acidic conditions or by oxidation, to provide the desired molecular weight. In an exemplary embodiment illustrated in FIG. 2, an alginic acid sodium salt starting material can be hydrolyzed by hydrochloric acid in a sodium bicarbonate buffer to create smaller copolymer block units.

In other embodiments, the polysaccharide can include chitin or chitosan. Chitosan is a linear polysaccharide composed of randomly distributed β-(1-4)-linked D-glucosamine (deacetylated unit) and N-acetyl-D-glucosamine (acetylated unit). Chitosan can be made by, for example, treating shrimp and other crustacean shells with the alkali sodium hydroxide. Synthesis of chitosan-retinoid conjugates can be prepared from the chitosan as shown, for example, in FIG. 6. In some embodiments, the chitosan can have a molecular weight of about 1000 to about 80,000 daltons, for example, about 1000 to about 60,000 daltons or about 3000 to about 10,000 daltons.

The retinoid that is used in the polysaccharide therapeutic conjugate composition can include any retinoid having a functional group capable of forming a covalent linkage with a monosaccharide subunit of a polysaccharide as described herein. Examples of retinoids can include vitamin A (retinol), a known physiologically active metabolite thereof and their synthetic derivatives. Physiologically active metabolites of retinol can include 11-cis-retinal, the visual chromophore, all-trans-retinoic acid, the 9-cis-isomer of all-trans-retinoic acid, and the retro-retinoids, anhydroretinol (AR) and 14-hydroxy-4,14-retro-retinol (14-HRR) and all-trans-13,14-dihydroxy-retinol.

In some embodiments, the retinoid is a retinal derivative, such as a synthetic retinal derivative. Synthetic retinal derivatives can include derivatives of 9-cis-retinal or 11-cis-retinal in which the aldehydic group in the polyene chain is converted to an ester, ether, alcohol, hemiacetal, acetal, oxime, as further described herein. Such synthetic retinal derivatives include 9-cis-retinyl esters, 9-cis-retinyl ethers, 9-cis-retinol, 9 cis-retinal oximes, 9-cis-retinyl acetals, 9-cis-retinyl hemiacetals, 11-cis-retinyl esters, 11-cis-retinyl ethers, 11-cis-retinol, 11-cis-retinyl oximes, 11-cis-retinyl acetals and 11-cis retinyl hemiacetals, as further described herein. The synthetic retinal derivative once conjugated to a polysaccharide can be controllably released from the polysaccharide-retinoid conjugate during digestion upon enteral administration to provide a natural or synthetic retinal, such as for example, 9-cis-retinal, 11-cis-retinal or a synthetic retinal analog thereof, such as those described herein or in International Application No. PCT/US04/07937, filed Mar. 15, 2004, (the disclosure of which is incorporated by reference herein).

An example of a synthetic retinal derivative can include a retinyl ester. In some embodiments, the retinyl ester is a 9-cis-retinyl ester or an 11-cis-retinyl ester. The ester substituent can include, for example, a carboxylic acid, such as a mono- or polycarboxylic acid. As used herein, a "polycarboxylic acid" is a di-, tri- or higher order carboxylic acid. In some embodiments, the carboxylic acid is a $C_1$-$C_{22}$, $C_2$-$C_{22}$, $C_3$-$C_{22}$, $C_1$-$C_{10}$, $C_2$-$C_{10}$, $C_3$-$C_{10}$, $C_4$-$C_{10}$, $C_4$-$C_8$, $C_4$-$C_6$ or $C_4$ monocarboxylic acid, or polycarboxylic acid.

Examples of carboxylic acids include acetic acid, propionic acid, butyric acid, valeric acid, caproic acid, caprylic acid, pelargonic acid, capric acid, lauric acid, oleic acid, stearic acid, palmitic acid, myristic acid or linoleic acid. The carboxylic acid also can be, for example, oxalic acid (ethanedioic acid), malonic acid (propanedioic acid), succinic acid (butanedioic), fumaric acid (butenedioic acid), malic acid (2-hydroxybutenedioic acid), glutaric acid (pentanedioic acid), adipic acid (hexanedioic acid), pimelic acid (heptanedioic), suberic acid (octanedioic), azelaic acid (nonanedioic acid), sebacic acid (decanedioic acid), citric acid, oxaloacetic acid, ketoglutaratic acid, or the like.

In some embodiments, the retinyl ester is a 9-cis-retinyl ester or an 11-cis-retinyl ester including a $C_3$-$C_{10}$ polycarboxylic acid substituent. (In this context, the terms "substituent" or "group" refer to a radical covalently linked to the terminal oxygen in the polyene chain). In another embodiment, the retinyl ester is a 9-cis-retinyl ester or an 11-cis retinyl ester including a $C_2$-$C_{22}$ or $C_3$-$C_{22}$ polycarboxylic acid substituent. The polycarboxylic acid substituent can be, for example, succinate, citrate, ketoglutarate, fumarate, malate or oxaloacetate. In another embodiment, the retinyl ester is a 9-cis-retinyl ester or an 11 cis-retinyl ester including a $C_3$-$C_{22}$ di-carboxylic acid (di-acid) substituent. In some embodiments, the polycarboxylic acid is not 9-cis-retinyl tartarate or 11-cis-retinyl tartarate. In some embodiments, the retinyl ester is not a naturally occurring retinyl ester normally found in the eye. In some embodiments, the retinyl ester is an isolated retinyl ester. As used herein, "isolated" refers to a molecule that exists apart from its native environment and is therefore not a product of nature. An isolated molecule may exist in a purified form or may exist in a non-native environment.

In another example, the retinal derivative can be a 9-cis-retinyl ester or ether of the following formula I:

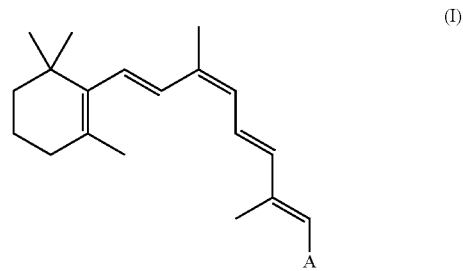

(I)

In some embodiments, A is $CH_2OR$, where R can be an aldehydic group, to form a retinyl ester. An aldehydic group can be a $C_1$ to $C_{24}$ straight chain or branched aldehydic group. The aldehydic group can also be a $C_1$ to $C_{14}$ straight chain or branched aldehydic group. The aldehydic group can be a $C_1$ to $C_{12}$ straight chain or branched aldehydic group, such as, acetaldehyde, propionaldehyde, butyraldehyde, valeraldehyde, hexanal, heptanal, octanal, nonanal, decanal, undecanal, dodecanal. R can be a $C_1$ to $C_{10}$ straight chain or branched aldehydic group, a $C_1$ to $C_8$ straight chain or branched aldehydic group, or a $C_1$ to $C_6$ straight chain or branched aldehydic group.

R can further be a carboxylate group of a dicarboxylic acid or other carboxylic acid (e.g., a hydroxyl acid) to form a retinyl ester (some of which are also referred to as retinoyl esters). The carboxylic acid can be, for example, oxalic acid (ethanedioic acid), malonic acid (propanedioic acid), succinic acid (butanedioic), fumaric acid (butenedioic acid), malic acid (2-hydroxybutenedioic acid), glutaric acid (pentanedioic acid), adipic acid (hexanedioic acid), pimelic acid (heptanedioic), suberic acid (octanedioic), azelaic acid (nonanedioic acid), sebacic acid (decanedioic acid), citric acid, oxaloacetic acid, ketoglutaratic acid, or the like.

R can also be an alkane group, to form a retinyl alkane ether. Examples of alkane groups include, $C_1$ to $C_{24}$ straight chain or branched alkyls, such as, methane, ethane, butane, isobutane, pentane, isopentane, hexane, heptane, octane or the like. For example, the alkane group can be a linear, iso-, sec-, tert- or other branched lower alkyl ranging from $C_1$ to $C_6$. The alkane group also can be a linear, iso-, sec-, tert- or other branched medium chain length alkyl ranging from $C_8$ to $C_{14}$. The alkane group also can be a linear, iso-, sec-, tert- or other branched long chain length alkyl ranging from $C_{16}$ to $C_{24}$.

R can further be an alcohol group, to form a retinyl alcohol ether. Examples of alcohol groups include linear, iso-, sec-, tert- or other branched lower alcohols ranging from $C_1$ to $C_6$, linear, iso-, sec-, tert- or other branched medium chain length alcohols ranging from $C_8$ to $C_{14}$, or linear, iso-, sec-, tert- or other branched long chain length alkyl ranging from $C_{16}$ to $C_{24}$.

The alcohol group can be, for example, methanol, ethanol, butanol, isobutanol, pentanol, hexanol, heptanol, octanol, or the like.

R can also be a carboxylic acid, to form a retinyl carboxylic acid ether.

Example of alcohol groups are linear, iso-, sec-, tert- or other branched lower carboxylic acids ranging from $C_1$ to $C_6$, linear, iso-, sec-, tert- or other branched medium chain length carboxylic acids ranging from $C_8$ to $C_{14}$, or linear, iso-, sec-, tert- or other branched long chain length carboxylic acids ranging from $C_{16}$ to $C_{24}$. Examples of carboxylic acid groups are example, acetic acid, propionic acid, butyric acid, valeric acid, caproic acid, caprylic acid, pelargonic acid, capric acid, lauric acid, oleic acid, stearic acid, palmitic acid, myristic acid, linoleic acid, succinic acid, fumaric acid or the like.

The retinyl derivative can be a retinyl hemiacetal, where A is CH(OH)OR. R can be any of the R groups set forth above in Formula I. R is typically a lower alkane, such as a methyl or ethyl group, or a $C_1$ to $C_7$ saturated and unsaturated, cyclic or acyclic alkane, with or without hetero atoms, as described herein.

The retinyl derivative can be a retinyl acetal, where A is CH(OR$_a$)OR$_b$. Each of R$_a$ and R$_b$ can be independently selected from any of the R groups set forth above in Formula I. R$_a$ and R$_b$ are typically a $C_1$ to $C_7$ saturated and unsaturated, cyclic or acyclic alkane, with or without hetero atoms, as described herein.

The retinyl derivative can also be a retinyl oxime, where A is CH:NOH or CH:NOR. R can be any of the R groups set forth above in Formula I. R is typically a hydrogen, or an alkane.

Examples of synthetic retinal derivatives include 9-cis-retinyl acetate, 9-cis-retinyl formate, 9-cis-retinyl succinate, 9-cis-retinyl citrate, 9-cis-retinyl 35 ketoglutarate, 9-cis-retinyl fumarate, 9-cis-retinyl malate, 9-cis-retinyl oxaloacetate, 9-cis-retinal oxime, 9-cis-retinal O-methyl oximes, 9-cis-retinal O-ethyl oximes, and 9-cisretinal methyl acetals and hemi acetals, 9-cis-retinyl methyl ether, 9-cis-retinyl ethyl ether, and 9-cis-retinyl phenyl ether.

In a related embodiment, the retinal derivative can be an 11-cis-retinyl ester or ether of the following formula II:

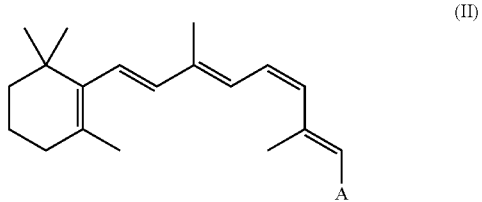

(II)

A can be any of the groups set forth above in Formula I.

Examples of synthetic retinal derivatives include, 11-cis-retinyl acetate, 11-cis-retinyl formate, 11-cis-retinyl succinate, 11-cis-retinyl citrate, 11-cis-retinyl ketoglutarate, 11-cis-retinyl fumarate, 11-cis-retinyl malate, 11-cis-retinal oxime, 11-cis-retinal O-methyl oxime, 1-cis-retinal O-ethyl oximes and 11-cis-retinal methyl acetals and hemi acetals, 11-cis-retinyl methyl ether, 11-cis-retinyl ethyl ether.

In additional embodiments, the synthetic retinal derivatives can be, for example, a derivative of a 9-cis-retinyl ester, a 9-cis-retinyl ether, an 11-cis-retinyl ester or an 11-cis-retinyl ethers, such as, an acyclic retinyl ester or ethers, a retinyl ester or ether with a modified polyene chain length, such as a trienoic or tetraenoic retinyl ester or ether; a retinyl ester or ether with a substituted polyene chain, such as alkyl, halogen or heteroatom-substituted polyene chains; a retinyl ester or ether with a modified polyene chain, such as a transor cis-locked polyene chain, or with, for example, allene or alkyne modifications; and a retinyl ester or ether with a ring modification(s), such as heterocyclic, heteroaromatic or substituted cycloalkane or cycloalkene rings.

The synthetic retinal derivative can be a retinyl ester or ether of the following formula III:

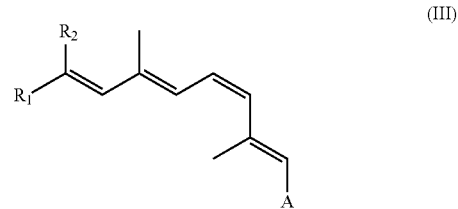

(III)

A can be any of the groups set forth above for formula (I). $R_1$ and $R_2$ can be independently selected from linear, iso-, sec-, tert- and other branched alkyl groups as well as substituted alkyl groups, substituted branched alkyl, hydroxyl, hydroalkyl, amine, amide, or the like. $R_1$ and $R_2$ can independently be lower alkyl, which means straight or branched alkyl with 1-6 carbon atom(s) such as methyl, ethyl, propyl, isopropyl, butyl, isobutyl, tert-butyl, pentyl, hexyl, or the like. Examples of substituted alkyls and substituted branch alkyls include alkyls, branchedalkyls andcyclo-alkyls substituted with oxygen, hydroxyl, nitrogen, amide, amine, halogen, heteroatom or other groups. Examples of heteroatoms include sulfur, silicon, and fluoro- or bromosubstitutions.

$R_1$ or $R_2$ also can be a cyclo-alkyl, such as hexane, cyclohexene, benzene as well as a substituted cycloalkyl. Suitable substituted cyclo-alkyls include, for example, cyclo-alkyls substituted with oxygen, hydroxyl, nitrogen, amide, amine, halogen, heteroatom and/or other groups. Suitable heteroatoms include, for example, sulfur, silicon, and fluoro- or bromo-substitutions.

The synthetic retinal derivative can also have a modified polyene chain length, such as the following formula IV:

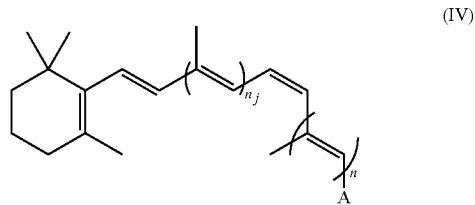

(IV)

A can be any of the groups set forth above for formula (I). The polyene chain length can be extended by 1, 2, or 3 alkyl, alkene or alkylene groups. According to formula (IV), each n and $n_j$ can be independently selected from 1, 2, or 3 alkyl, alkene or alkylene groups, with the proviso that the sum of the n and $n_j$ is at least 1.

The synthetic retinal derivative can also have a substituted polyene chain of the following formula V:

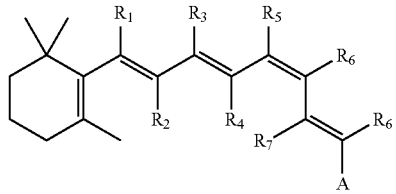

(V)

A can be any of the groups set forth above for formula (1). Each of $R_1$ to $R_8$ can be independently selected from hydrogen, alkyl, branched alkyl, cyclo-alkyl, halogen, a heteratom, or the like. Examples of alkyls include methyl, ethyl, propyl, substituted alkyl (e.g., alkyl with hydroxyl, hydroalkyl, amine, amide) or the like. Examples of branched alkyls are isopropyl, isobutyl, substituted branched alkyl, or the like. Examples of cyclo-alkyls are cyclohexane, cycloheptane, and other cyclic alkanes as well as substituted cyclic alkanes, such as substituted cyclohexane or substituted cycloheptane. Examples of halogens are bromine, chlorine, fluorine, or the like. Examples of heteroatoms are, sulfur, silicon, and fluoro- or bromo-substitutions. Examples of substituted alkyls, substituted branch alkyls and substituted cyclo-alkyls include, alkyls, branched alkyls and cyclo-alkyls substituted with oxygen, hydroxyl, nitrogen, amide, amine, halogen, heteroatom or other groups.

For example, the synthetic retinal derivative can be selected from the following: a 9-ethyl-11-cis-retinyl ester, ether, oxime, acetal or hemiacetal; a 7-methyl-11-cis-retinyl ester, ether, oxime, acetal or hemiacetal; a 13-desmethyl-11cis-retinyl ester, ether, oxime, acetal or hemiacetal; an 11-cis 10-F-retinyl ester, ether, oxime, acetal or hemiacetal; an 11-cis-10-$C_1$-retinyl ester, ether, oxime, acetal or hemiacetal; an 11-cis-10-methyl-retinyl ester, ether, oxime, acetal or hemiacetal; an 11-cis-10-ethyl-retinyl ester, ether, oxime, acetal or hemiacetal; a 9-cis-10-F-retinyl ester, ether, oxime, acetal or hemiacetal; a 9-cis-10-$C_1$-retinyl ester, ether, oxime, acetal or hemiacetal; a 9-cis-10-methyl-retinyl ester, ether, oxime, acetal or hemiacetal; a 9-cis-10-ethyl-retinyl ester, ether, oxime, acetal or hemiacetal; an 11-cis-12-F-retinyl ester, ether, oxime, acetal or hemiacetal; an 11-cis-12-$C_1$-retinyl ester, ether, oxime, acetal or hemiacetal; an 11-cis-12 methyl-retinyl ester, ether, oxime, acetal or hemiacetal; an 11-cis 10-ethyl-retinyl ester, ether, oxime, acetal or hemiacetal; a 9-cis-12-F-retinyl ester, ether, oxime, acetal or hemiacetal; a 9-cis-12-$C_1$-retinyl ester, ether, oxime, acetal or hemiacetal; a 9-cis-12-methyl-retinyl ester, ether, oxime, acetal or hemiacetal; an 11-cis-14-F-retinyl ester, ether, oxime, acetal or hemiacetal; an 11-cis-14-methyl-retinyl ester, ether, oxime, acetal or hemiacetal; an 11-cis-14-ethylretinyl ester, ether, oxime, acetal or hemiacetal; a 9-cis-14-Fretinyl ester, ether, oxime, acetal or hemiacetal; a 9-cis-14 methyl-retinyl ester, ether, oxime, acetal or hemiacetal; a 9-cis-14-ethyl-retinyl ester, ether, oxime, acetal or hemiacetal; or the like.

The synthetic retinal derivative further can have a modified ring structure. Examples include, derivatives containing ring modifications, aromatic analogs and heteroaromatic analogs of the following formulae VI, VII and VIII, respectively:

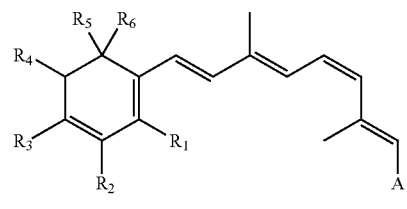

(VI)

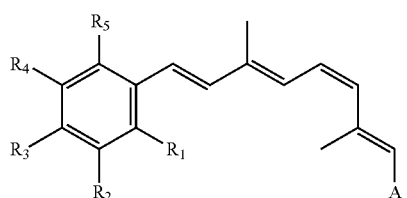

(VII)

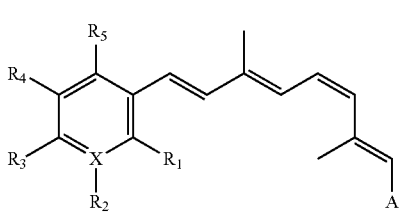

(VIII)

A can be any of the groups set forth above for formula (I). Each of $R_1$ to $R_6$, as applicable, can be independently selected from hydrogen, alkyl, substituted alkyl, hydroxyl, hydroalkyl, amine, amide, halogen, a heteratom, or the like. Examples of alkyls are methyl, ethyl, propyl, isopropyl, butyl, isobutyl or the like. Examples of halogens are bromine, chlorine, fluorine, or the like. Examples of heteroatoms are sulfur, silicon, or nitrogen. In formulae VII, X can be, for example, sulfur, silicon, nitrogen, fluoro- or bromo substitutions. Similarly, 9-cis-synthetic retinal derivatives containing ring modifications, aromatic analogs and heteroaromatic analogs of those shown in formulae VI, VII and VIII are contemplated.

The synthetic retinal derivative also can have a modified polyene chain. Examples of derivatives include those with a trans/cis locked configuration, 6s-locked analogs, as well as modified allene, alkene, alkyne or alkylene groups in the polyene chain. In one example, the derivative is an 11-cis-locked analog of the following formula IX:

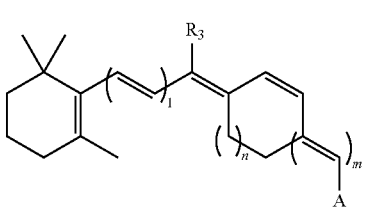

(IX)

A can be any of the groups set forth above for formula (1). $R_3$ can be, for example, hydrogen, methyl or other lower alkane or branch alkane. n can be 0 to 4. m plus 1 equals 1, 2 or 3.

In one embodiment, the synthetic retinal derivative can be an 11-cis-locked analog of the following formula X:

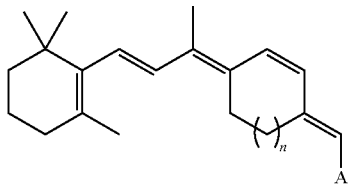

(X)

n can be 1 to 4. A can be any of the groups set forth above for formula (I).

The synthetic retinal derivative is a 9, 11, 13-tri-cis-7-ring retinyl ester or ether, an 11,13-di-cis-7-ring retinyl ester or ether, an 11-cis-7-ring retinyl ester or ether or a 9,11-di-cis-7-ring retinyl ester or ether.

In another example, the synthetic retinal derivative is a 6s-locked analog of formula XI. A can be any of the groups set forth above for formula (1). $R_1$ and $R_2$ can be independently selected from hydrogen, methyl and other lower alkyl and substituted lower alkyl. $R_3$ can be independently selected from an alkene group at either of the indicated positions.

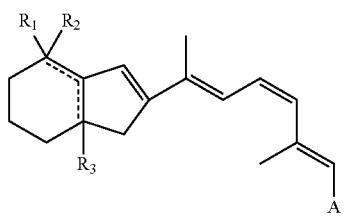

(XI)

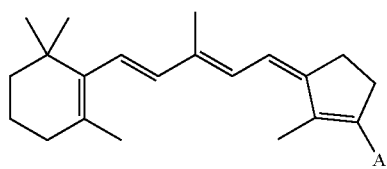

(XII)

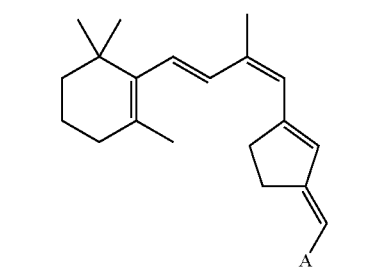

(XIII)

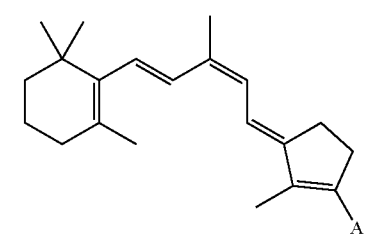

(XIV)

The synthetic retinal derivative can be a 9-cis-ring-fused derivative, such as those shown in formulae XII-XIV. A can be any of the groups set forth above for formula (I). The synthetic retinal derivative also can be of the following formula XV or XVI.

The synthetic retinal derivative also can be of the following formula XV or XVI.

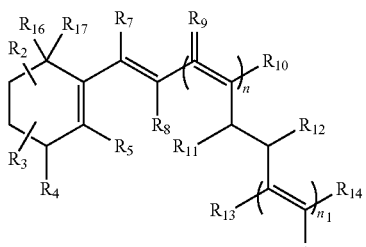

(XV)

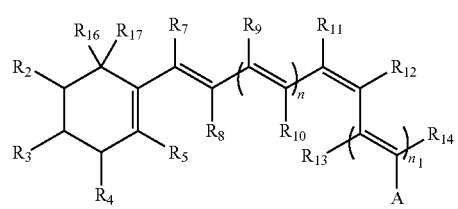

(XVI)

A can be any of the groups set forth above for formula (1). Each of $R_2$ to $R_5$, $R_7$ to $R_{14}$, $R_{16}$ and $R_{17}$ can be absent or independently selected from hydrogen, alkyl, branched alkyl, halogen, hydroxyl, hydroalkyl, amine, amide, a heteratom, or the like. Alkyls include, for example, methyl, ethyl, propyl, substituted alkyl (e.g., alkyl with hydroxyl, hydroalkyl, amine, amide), or the like. Branched alkyls can be, for example, isopropyl, isobutyl, substituted branched alkyl, or the like. Halogens include, for example, bromine, chlorine, fluorine, or the like. Heteroatoms include, for example, sulfur, silicon, and fluoro- or bromo substitutions. Substituted alkyls and substituted branch alkyls include, for example, alkyls and branched alkyls substituted with oxygen, hydroxyl, nitrogen, amide, amine, halogen, heteroatom or other groups. Each of n and $n_1$ can be independently selected from 1, 2, or 3 alkyl, alkene or alkylene groups, with the proviso that the sum of the N and $n_1$ is at least 1. In addition, $R_3$-$R_4$ and/or $R_2$-$R_{16}$ can comprise an alkene group in the cyclic carbon ring, in which case $R_{17}$ is absent. $R_{10}$ and $R_{13}$ together can form a cycloalkyl, such as a five, six, seven or eight member cyclo-alkyl or substituted cycloalkyl, such as, for example, those shown in Formulae IX, X, XII, XIII and XIV.

Methods of making synthetic retinals and derivatives are disclosed in, for example, the following references: *Anal. Biochem.* 272:232-42 (1999); *Angew. Chem.* 36:2089-93 (1997); *Biochemistry* 14:3933-41 (1975); *Biochemistry* 21:384-93 (1982); *Biochemistry* 28:2732-39 (1989); *Biochemistry* 33:408-16 (1994); *Biochemistry* 35:6257-62 (1996); *Bioorganic Chemistry* 27:372-82 (1999); *Biophys. Chem.* 56:31-39 (1995); *Biophys. J.* 56: 1259-65 (1989); *Bio-phys. J.* 83:3460-69 (2002); *Chemistry* 7:4198-204 (2001); *Chemistry* (Europe) 5:1172-75 (1999); *FEBS* 158:1 (1983); *J. Am. Chem. Soc.* 104:3214-16 (1982); *J. Am. Chem. Soc.* 108:6077-78 (1986); *J. Am. Chem. Soc.* 109: 6163 (1987); *J. Am. Chem. Soc.* 112:7779-82 (1990); *J. Am. Chem. Soc.* 119:5758-59 (1997); *J. Am. Chem. Soc.* 121: 5803-04 (1999); *J. American Chem. Soc.* 123:10024-29 (2001); *J. American Chem. Soc.* 124:7294-302 (2002); *J. Biol. Chem.* 276:26148-53 (2001); *J. Bioi. Chem.* 277:

42315-24 (2004); *J. Chem. Soc.-Perkin T.* 1:1773-77 (1997); *J. Chem. Soc.-Perkin T* 1:2430-39 (2001); *J. Org. Chem.* 49:649-52 (1984); *J. Org. Chem.* 58:3533-37 (1993); *J. Physical Chemistry B* 102:2787-806 (1998); *Lipids* 8:558-65; *Photochem. Photobiol.* 13:259-83 (1986); *Photochem. Photobiol.* 44:803-07 (1986); *Photochem. Photobiol.* 54:969-76 (1991); *Photochem. Photobiol.* 60:64-68 (1994); *Photochem. Photobiol.* 65:1047-55 (1991); *Photochem. Photobiol.* 70:111-15 (2002); *Photochem. Photobiol.* 76:606 615 (2002); *Proc. Natl. Acad. Sci. USA* 88:9412-16 (1991); *Proc. Natl. Acad Sci. USA* 90:4072 76 (1993); *Proc. Natl. Acad. Sci. USA* 94:13442-47 (1997); and *Proc. R. Soc. Lond Series B, Biol. Sci.* 233(1270): 55-76 (1988) (the disclosures of which are incorporated by reference herein).

Retinyl esters can be formed by methods known in the art such as, for example, by acid-catalyzed esterification of a retinol with a carboxylic acid, by reaction of an acyl halide with a retinol, by transesterification of a retinyl ester with a carboxylic acid, by reaction of a primary halide with a carboxylate salt of a retinoic acid, by acid-catalyzed reaction of an anhydride with a retinol, or the like. In an example, retinyl esters can be formed by acid-catalyzed esterification of a retinol with a carboxylic acid, such as, acetic acid, propionic acid, butyric acid, valerie acid, caproic acid, caprylic acid pelargonic acid, capric acid, lauric acid, oleic acid, stearatic acid, palmitic acid, myristic acid, linoleic acid, succinic acid, fumaric acid or the like. In another example, retinyl esters can be formed by reaction of an acyl halide with a retinol (see, e.g., Van Hooser et al., *Proc. Natl. Acad. Sci. USA,* 97:8623-30 28 (2000)). Suitable acyl halides include, for example, acetyl chloride or the like.

Retinyl ethers can be formed by methods known in the art, such as for example, reaction of a retinol with a primary alkyl halide.

In some embodiment, the retinoid can include a trans-retinoid or a cis-retinoid. Trans-retinoids can be isomerized to cis-retinoids by exposure to UV light. For example, all-trans-retinal, all-transretinol, all-trans-retinyl ester or all-trans-retinoic acid can be isomerized to 9-cis-retinal, 9-cis-retinol, 9-cis-retinyl ester or 9-cis-retinoic acid, respectively. Trans-retinoids can be isomerized to 9-cis-retinoids by, for example, exposure to a UV light having a wavelength of about 365 nm, and substantially free of shorter wavelengths that cause degradation of cis-retinoids, as further described herein.

Retinyl acetals and hemiacetals can be prepared, for example, by treatment of 9-cis- and 11-cis-retinals with alcohols in the presence of acid catalysts. Water formed during reaction is removed, for example by $Al_2O_3$ of a molecular sieve.

Retinyl oximes can be prepared, for example, by reaction of a retinal with hydroxylamine, O-methyl- or O-ethylhydroxylamine, or the like. In some embodiments, a retinoid can further include a transition state inhibitor of RPE65. For example, the amide ester retinylamide.

In some embodiments, the carboxylate anion of a polysaccharide monomer subunit can act as an alkylating agent with a retinoid having an alkyl to form covalent ester linkages. In the case that an alkyl chloride is used, an iodide salt can catalyze the reaction. The carboxylate salt may be generated in situ from a carboxylic acid. This reaction can suffer from anion availability problems and, therefore, can benefit from the addition of phase transfer catalysts and/or highly polar aprotic solvents such as dimethylformamide (DMF) or dichloromethane (DCM).

Therefore, in another embodiment, a method for preparing a composition which comprises a polysaccharide covalently linked to at least one retinoid includes reacting the at least one retinoid with a chlorinating agent to provide at least one retinoid having a primary chloride functional group. The method further includes reacting the resultant retinoid chloride with a monosaccharide subunit of the polysaccharide having a carboxylate functional group in the presence of a phase transfer catalyst. The phase transfer catalyst catalyzes the formation of a hydrolysable carboxylic ester covalent linkage between the monosaccharide subunit and the retinoid. An example of a phase transfer catalyst for use in the present invention can include a quaternary ammonium salt, such as Aliquat 336 (also known as Starks' catalyst).

Figure 4:
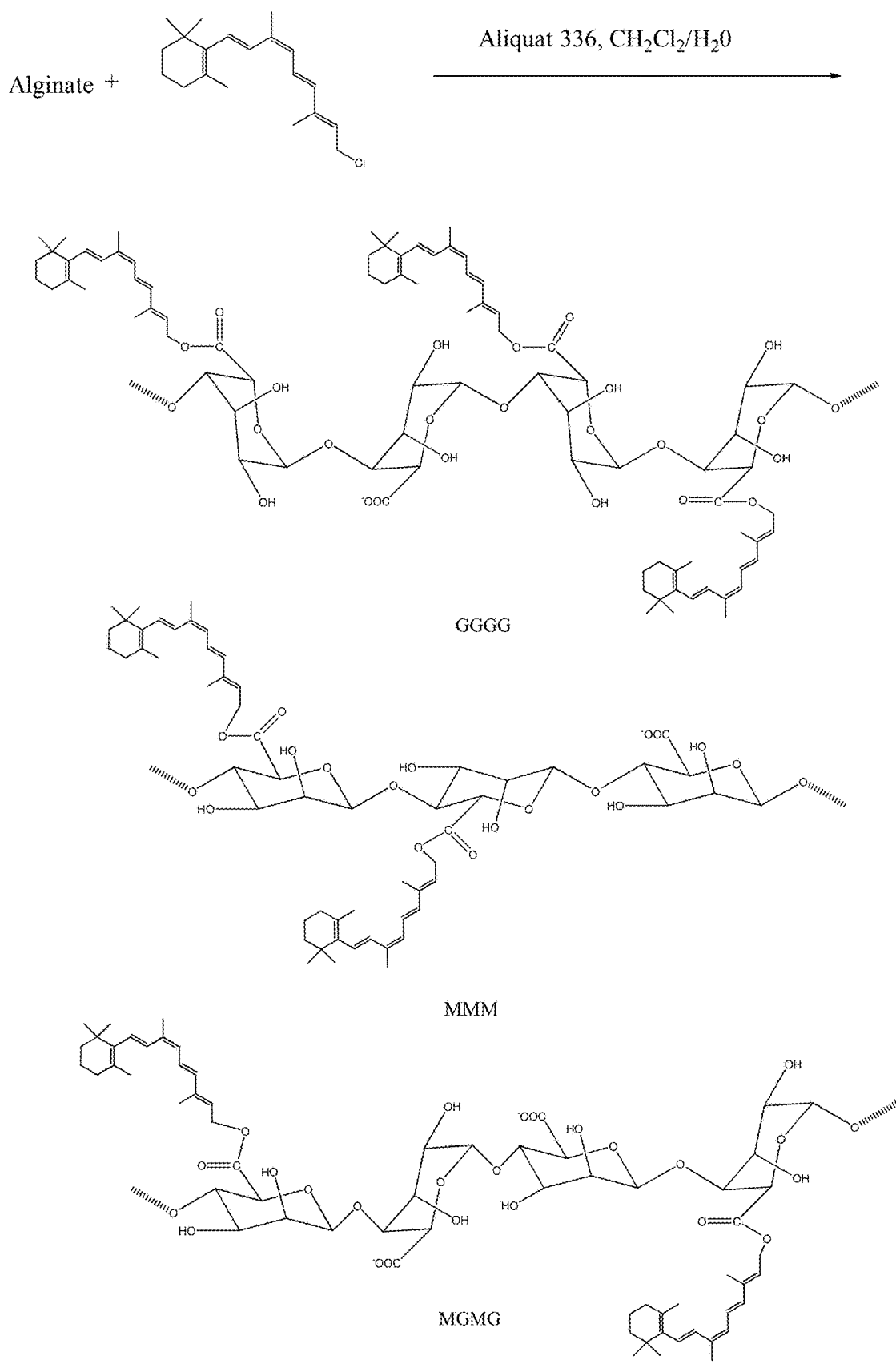
FIG. 4 is a schematic illustration showing a synthesis scheme of alginic acid-retinoid conjugates using the phase transfer catalyst Aliquat 336 in a polar solvent.
Figure 5:
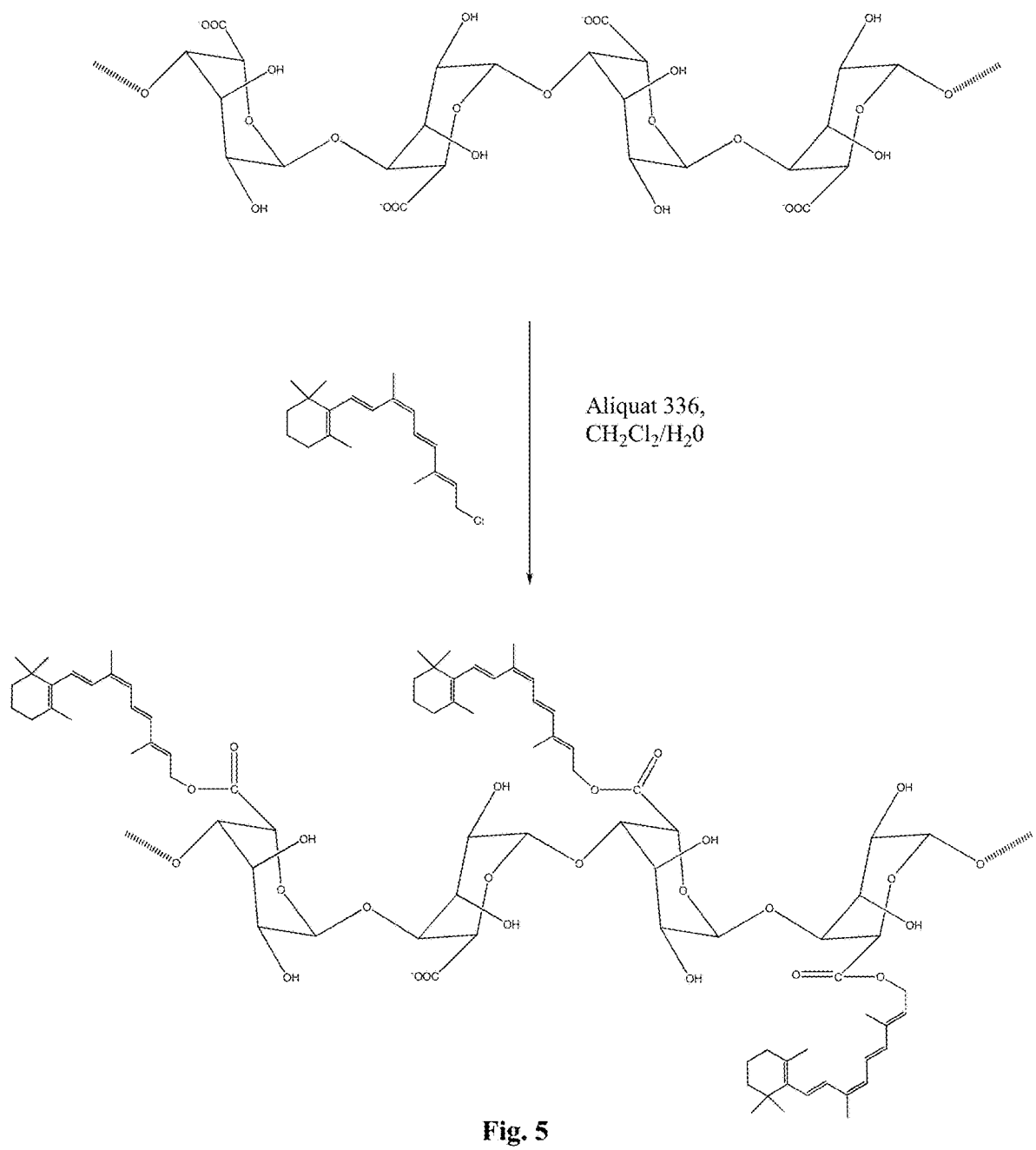
FIG. 5 is a schematic illustration showing a synthesis of guluronic acid 9-cis retinol conjugate from alginic acid and 9-cis retinal chloride using the phase transfer catalyst Aliquat 336 in a polar solvent.

In the presence of a phase transfer catalyst, a retinoid having a terminal alkyl chloride can form a carboxylic ester covalent bond with the carboxylate ion of either a β-D-mannuronate (M) or α-L-guluronate (G) subunit of an alginate polymer. Thus, in some embodiments, retinoids with a primary halide group can be covalently linked directly to a caboxylate ion of a monosaccharide subunit. In an exemplary embodiment, illustrated in FIG. 4, a 9-cis retinal chloride is conjugated to alginate in the presence of Aliquat 336 phase transfer catalyst and solvent solution through a carboxylic ester linkage.

However, because few retinoids have halide groups, the more applicable means of providing a degradeable covalent linkage is to first halogenate a retinoid with a holgenating agent to synthesize a corresponding retinal halide. For example, alkyl halides can be prepared by reacting alcohols with a halogenating agent. An exemplary method includes reacting a retinoid having a terminal hydroxyl functional group (e.g., 9-cis retinol, 11-cis retinol or derivatives thereof), with a chlorinating agent to synthesize a corresponding retinal halide (9-cis retinal chloride, 11-cis retinal chloride or derivatives thereof). The terminal —OH functional group can be converted into an alkyl chloride by reacting the —OH functional group with a chlorinating agent using an internal nucleophilic substitution reaction. In each case the —OH functional group reacts first as a nucleophile, attacking the electrophilic center of the chlorinating agent. A displaced chloride ion then completes the substitution displacing the leaving group.

Figure 3:
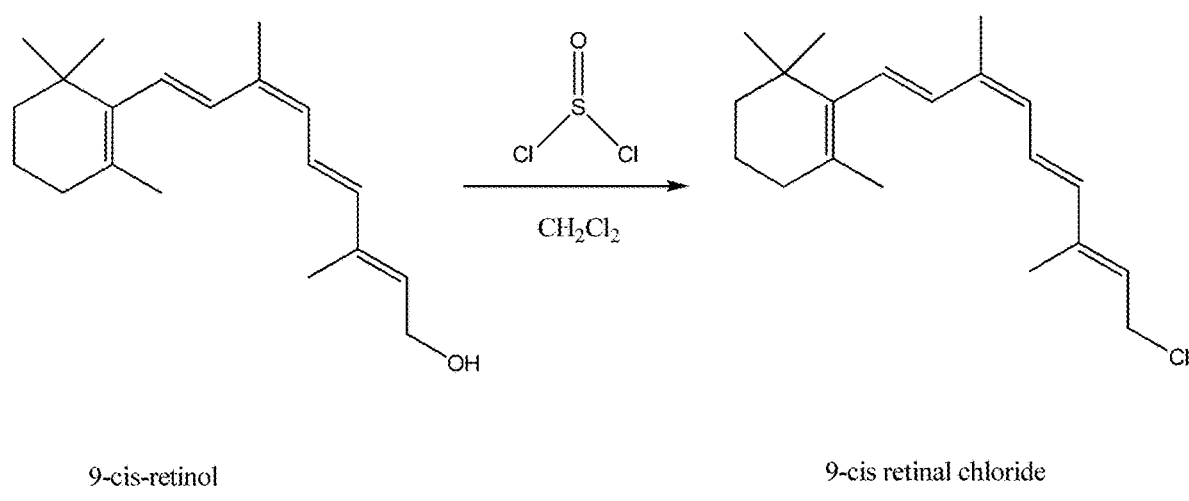
FIG. 3 is a schematic illustration showing a synthesis scheme of 9-cis retinal chloride from 9-cis retinol using the chlorinating agent thionyl dichloride in solvent.

An example of a chlorinating agent can include thionyl chloride ($SOCl_2$), phosphorous trichloride ($PCl_3$), or phosphorous pentachloride ($PCl_5$). In certain embodiments, thionyl chloride is especially convenient, because the byproducts are gaseous. In an exemplary embodiment illustrated in FIG. 3, 9-cis retinal chloride can be synthesized from 9-cis retinol using the chlorinating agent thionyl dichloride in the presence of an aprotic solvent such as dichloromethane (DCM).

It is further contemplated that these approaches for covalently linking a polysaccharide to a retinoid through an ester linkage can be extended to prepare additional non-retinoid polysaccharide therapeutic conjugate compositions for use where sustained delivery of a therapeutic agent is desirable.

The polysaccharide retinoid conjugates described herein can be administered as prodrugs to give a sustained release of the active retinoid over time. Advantages thereof include a decrease in toxicity effects of the free retinoid, economizing of the amount of retinoid needed due to an increase in circulation time and facilitating solubilization of hydrophobic retinoids. The particular polysaccharide and molecular weight thereof can be selected to suit the particular application, of which retinopathy therapeutic applications are of particular interest.

Thus, in another embodiment of the application, a method for treating an ocular disorder or ophthalmic disease in a subject includes administering to the subject a therapeutically effective amount of a composition that includes a polysaccharide and at least one retinoid. The at least one retinoid can be linked to at least one monosaccharide subunit of the polysaccharide with a covalent linkage. The linkage can be degradable by hydrolysis during digestion of the composition to provide sustained delivery of the retinoid upon enteral administration of the composition to a subject.

In some embodiments, a therapeutic polysaccharide conjugate composition described herein can be administered to a subject for treating, curing, preventing, ameliorating the symptoms of, or slowing, inhibiting, or stopping the progression of ocular or ophthalmic diseases or disorders. Representative ophthalmic diseases and disorders include, but are not limited to, macular degeneration, glaucoma, diabetic retinopathy, retinal detachment, retinal blood vessel occlusion, retinitis pigmentosa, autosomal dominant retinitis pigmentosa (ADRP), optic neuropathy, inflammatory retinal disease, diabetic maculopathy, hemorrhagic retinopathy, retinopathy of prematurity, optic neuropathy, proliferative vitreoretinopathy, retinal dystrophy, ischemia-reperfusion related retinal injury, hereditary optic neuropathy, metabolic optic neuropathy, Leber congenital amaurosis (LCA) including LCA arising from mutations in the LRAT and RPE65 genes, Stargardt's macular dystrophy, Sorsby's fundus dystrophy, Fundus albipunctatus, congenital stationary nightblindness (CSNB), Best disease, uveitis, age-related retinal dysfunction, a retinal injury, a retinal disorder associated with Parkinson's disease, a retinal disorder associated with viral infection, a retinal disorder related to light overexposure, and a retinal disorder associated with AIDS, a retinal disorder associated with Alzheimer's disease, and a retinal disorder associated with multiple sclerosis.

Vitamin A, retinol, plays essential roles in many biological processes including vision, immunity, growth, development, and cellular differentiation. Therefore, in some embodiments, the polysaccharide retinoid conjugates described herein can be administered to a subject for retinoid replacement, supplementing the levels of endogenous retinoid. For example, a polysaccharide retinoid conjugate of the present invention can be administered to a subject having a vitamin A deficiency (VAD). In some embodiments, a polysaccharide retinoid conjugate described herein can be administered to a subject for the pharmacological inhibition of the retinoid cycle.

The polysaccharide retinoid conjugates can be converted directly or indirectly into a retinal or a synthetic retinal analog by degrading the covalent linkage between the polysaccharide and the retinoid during digestion. Thus, in some embodiments, the compositions can be described as a pro-drug, which upon enteral administration and metabolic transformation is converted into a therapeutic retinoid such as 9-cis-retinal, 11-cis-retinal or a synthetic retinal analog thereof. Metabolic transformation can occur, for example by acid hydrolysis, esterase activity, acetyltransferase activity, dehydrogenase activity, or the like. In some embodiments, the compositions described herein when administered to a subject enterally allow for longer persistence in the digestive track and sustained delivery or sustained plasma level.

In some embodiments, methods of using a polysaccharide retinoid conjugate are provided to restore or stabilize photoreceptor function, or to ameliorate photoreceptor loss, in a vertebrate visual system. A synthetic retinal derivative can be administered to a subject having a retinoid deficiency (e.g., a deficiency of 11-cis-retinal), an excess of free opsin, an excess of retinoid waste (e.g., degradation) products or intermediates in the recycling of all-trans-retinal, or the like. The vertebrate eye typically comprises a wild-type opsin protein. Methods of determining endogenous retinoid levels in a vertebrate eye, and a deficiency of such retinoids, are disclosed in, for example, U.S. Provisional Patent Application No. 60/538,051 (filed Feb. 12, 2004) (the disclosure of which is incorporated by reference herein). Other methods of determining endogenous retinoid levels in a vertebrate eye, and a deficiency of such retinoids, include for example, analysis by high pressure liquid chromatography (HPLC) of retinoids in a sample from a subject. For example, retinoid levels or a deficiency in such levels can be determined from a blood sample from a subject.

A blood sample can be obtained from a subject and retinoid types and levels in the sample can be separated and analyzed by normal phase high pressure liquid chromatography (HPLC) (e.g., with a Agilent HP1100 HPLC and a Beckman, Ultrasphere-Si, 4.6 mm×250 mm column using 10% ethyl acetate/90% hexane at a flow rate of 1.4 ml/minute). The retinoids can be detected by, for example, detection at 325 nm using a diode-array detector and HP ChemstationA.03.03 software. A deficiency in retinoids can be determined, for example, by comparison of the profile of retinoids in the sample with a sample from a control subject (e.g., a normal subject). As used herein, absent, deficient or depleted levels of endogenous retinoid, such as 11-cis-retinal, refer to levels of endogenous retinoid lower than those found in a healthy eye of a vertebrate of the same species.

The polysaccharide retinoid conjugates can be administered prophylactically or therapeutically to a vertebrate. As used herein, "prophylactic" and "prophylactically" refer to the administration of a polysaccharide retinoid conjugate to prevent deterioration or further deterioration of the vertebrate visual system, as compared with a comparable vertebrate visual system not receiving the synthetic retinal derivative.

The term "restore" refers to a long-term (e.g., as measured in weeks or months) improvement in photoreceptor function in a vertebrate visual system, as compared with a comparable vertebrate visual system not receiving the polysaccharide retinoid conjugate. The term "stabilize" refers to minimization of additional degradation in a vertebrate visual system, as compared with a comparable vertebrate visual system not receiving the polysaccharide retinoid conjugate.

In one embodiment, the subject is characterized as having Leber Congenital Amaurosis ("LCA"). This disease is a very rare childhood condition that effects children from birth or shortly thereafter. It affects both rods and cones in the eye. For example, certain mutations in the genes encoding RPE65 and LRAT proteins are involved in LCA. Mutations in both genes result in a person's inability to make 11-cis-retinal in adequate quantities. Thus, 11-cis-retinal is either absent or present in reduced quantities. In RPE65-defective individuals, retinyl esters build up in the RPE. LRAT-defective individuals are unable to make esters and subsequently secrete any excess retinoids. For LCA, a polysaccharide retinoid conjugate can be used to replace the absent or depleted 11-cis-retinal.

In another embodiment, the vertebrate eye is characterized as having Retinitis Punctata Albesciens. This disease is a form of Retinitis Pigmentosa that exhibits a shortage of 11-cis-retinal in the rods. A polysaccharide retinoid conjugate can be used to replace the absent or depleted 11-cis retinal.

In another embodiment, the vertebrate eye is characterized as having Congenital Stationary Night Blindness ("CSNB") or Fundus Albipunctatus. This group of diseases is manifested by night blindness, but there is not a progressive loss of vision as in the Retinitis Pigmentosa. Some forms of CSNB are due to a delay in the recycling of 11-cis-retinal. Fundus Albipunctatus until recently was thought to be a special case of CSNB where the retinal appearance is abnormal with hundreds of small white dots appearing in the retina. It has been shown that this is also a progressive disease, although with a much slower progression than Retinitis Pigmentosa. It is caused by a gene defect that leads to a delay in the cycling of 11-cis-retinal. Thus, a polysaccharide retinoid conjugate(s) can be administered to restore photoreceptor function by retinoid replacement.

In yet another embodiment, the vertebrate eye is characterized as having age-related macular degeneration ("AMD"). AMD can be wet or dry forms. In AMD, vision loss occurs when complications late in the disease either cause new blood vessels to grow under the retina or the retina atrophies. Without intending to be bound by any particular theory, excessive production of waste products from the photoreceptors may overload the RPE. This is due to a shortfall of 11-cis-retinal available to bind opsin. Free opsin is not a stable compound and can spontaneously cause firing of the biochemical reactions of the visual cascade without the addition of light.

Administration of a polysaccharide retinoid conjugate to the vertebrate eye can reduce the deficiency of 11-cis-retinal and quench spontaneous misfiring of the opsin. Administration of a polysaccharide retinoid conjugate can lessen the production of waste products and/or lessen drusen formation, and reduce or slow vision loss (e.g., choroidal neovascularization and/or chorioretinal atrophy).

In other embodiments, a polysaccharide retinoid conjugate is administered to an aging subject, such as a human. As used herein, an aging human subject is typically at least 45, or at least 50, or at least 60, or at least 65 years old. The subject has an aging eye, which is characterized as having a decrease in night vision and/or contrast sensitivity. Excess unbound opsin randomly excites the visual transduction system. This creates noise in the system and thus more light and more contrast are necessary to see well. Quenching these free opsin molecules with a therapeutic retinoid disassociated from a polysaccharide retinoid conjugate will reduce spontaneous misfiring and increase the signal to noise ratio, thereby improving night vision and contrast sensitivity.

The subject can include vertebrates, such as, human and non-human vertebrates. Examples of non-human vertebrates include mammals, such as dogs (canine), cats (feline), horses (equine) and other domesticated animals.

The polysaccharide retinoid conjugates can be substantially pure, in that it contains less than about 5% or less than about 1%, or less than about 0.1%, of other retinoids. In some embodiments, a combination of polysaccharide retinoid conjugates described herein can be administered to a subject.

Polysaccharide retinoid conjugates can be formulated, for example, as pharmaceutical compositions for oral administration, local administration to the eye and/or for intravenous, intramuscular administration.

Polysaccharide retinoid conjugates can be formulated for administration using pharmaceutically acceptable vehicles as well as techniques routinely used in the art. A vehicle can be selected according to the solubility of the polysaccharide retinoid conjugate. Examples of pharmaceutical compositions include those that are administrable enterally or orally.

Examples of oral dosage forms include tablets, pills, sachets, or capsules of hard or soft gelatin, methylcellulose or of another material easily dissolved in the digestive tract. Examples of nontoxic solid carriers can include pharmaceutical grades of mannitol, lactose, starch, magnesium stearate, sodium saccharin, talcum, cellulose, glucose, sucrose, magnesium carbonate, and the like. (See, e.g., Remington "Pharmaceutical Sciences", 17 Ed., Gennaro (ed.), Mack Publishing Co., Easton, Pa. (1985).)

The doses of the polysaccharide retinoid conjugates can be selected depending on the clinical status, condition and age of the subject, dosage form and the like.

For example, oral doses can typically range from about 0.01 to about 1000 mg, one to four times, or more, per day, week, or month. An exemplary dosing range for oral administration is from about 10 to about 250 mg one to three times per week.

Example

We designed a polysaccharide therapeutic conjugate composition for the sustained release of 9-cis-retinyl esters to treat animal models of human retinal diseases, such as LCA. We found that administration of 9-cis-R-Ac by oral gavage improves visual function and preserves retinal morphology in LCA mouse models with LRAT and RPE65 deficiency, that is, $Lrat^{-/-}$ and $Rpe65^{-/-}$ mice. We also found that 9-cis-retinoid concentrations in plasma increased rapidly to high levels after gavage and then dropped markedly to low levels 5 hours after oral administration. Unless initial high drug blood levels are unfavorable, this pharmacokinetic property could be beneficial because it relates to the therapeutic window, especially for drugs targeting peripheral tissues such as the retina through protein-mediated and protein-independent transport systems. A bolus dose could also establish a reversible depot of the drug in other tissues, thereby reducing the need for frequent dosing. For example, we observed that a single dose of 9-cis-retinal to $Rpe65^{-/-}$ mice rescued visual function for months, even when animals were kept under laboratory lighting conditions.

Nonetheless, sustained therapeutic dosing methods can hold numerous advantages over bolus dosing, including a lower risk of toxicity and an increased duration of therapeutic efficacy. In the case of retinoid supplementation therapy, it provides an additional source for the drug. The retina poses unique challenges for sustained therapeutic dosing because of its anatomic isolation. Frequent injections of compounds directly into the vitreous cavity are associated with complications, such as retinal detachment, hemorrhage, uveitis, endophthalmitis, and infections. Therefore, delivery of hydrophobic 9-cis-retinoids directly by this route presents an additional concern.

The $Lrat^{-/-}$ mouse provides an excellent model for human LCA because it exhibits early-onset, slowly progressive severe retinal degeneration. Because the RPE of $Lrat^{-/-}$ mice is devoid of all-trans-retinol and all-trans-retinyl esters, the photoreceptors lack functional rhodopsin, and electroretinographic (ERG) responses are dramatically attenuated. $Lrat^{-/-}$ mice have been used to test the efficacy of pharmacologic agents such as 9-cis-R-Ac and a standard gene replacement technique. Moreover, lack of LRAT in the liver and other tissues has no apparent deleterious effects. These mice constitute an important experimental model for retinoid metabolism and vitamin A deprivation as well as for human LCA.

Figure 6:
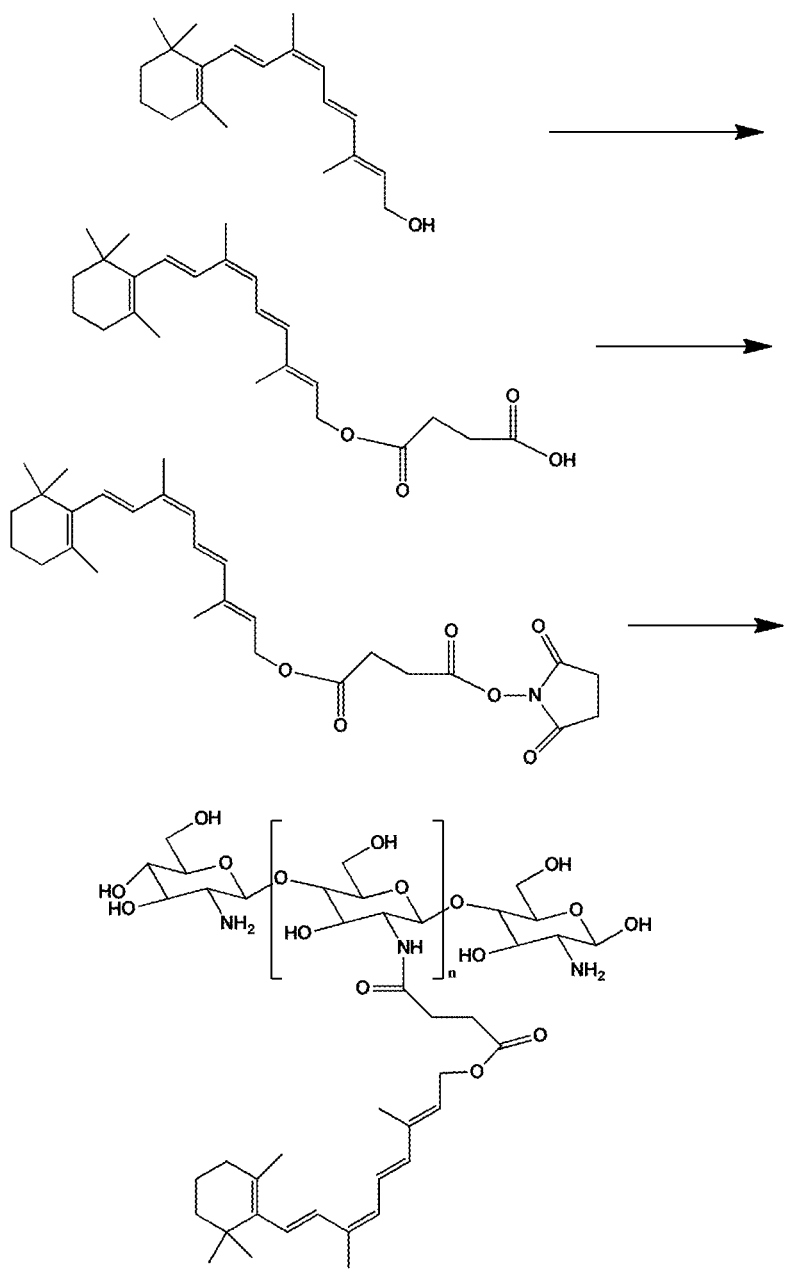
FIG. 6 is schematic illustration showing the synthesis of chitosan-9-cis-retinol conjugates.

To achieve sustained release of 9-cis-retinoids, we designed a polysaccharide therapeutic conjugate composition that uses a chitosan, which is covalently linked to 9-cis-retinoids. The covalent linkage is hydrolyzable upon enteral administration to provide sustained delivery of the 9-cis-retinoids to the eye of subject at least 24 hours (e.g., 24 hours to 1 week) after enteral administration. The polysaccharide therapeutic conjugate composition slows drug release upon enteral administration and thus blunts an initial excessive drug release. This drug-delivery system can maintain optimal therapeutic drug levels, reduce side effects by sustained drug release, and improve patient compliance by decreasing the frequency of drug administration in a minimally invasive manner. To show sustained retinoid release could be achieved by using a polysaccharide therapeutic conjugate composition and rescue visual function, we prepared a chitosan-retinoid conjugate as shown in FIG. 6, investigated 9-cis-retinoid release from this composition in vivo, and evaluated its therapeutic efficacy in retinas of $Lrat^{-/-}$ mice.

Animals

Lrat−/− mice were generated and genotyped and 5-week-old animals of both sexes were used for the experiments described. All mice were housed in the animal facility at the School of Medicine, Case Western Reserve University, where they were maintained on a standard diet under a 12-hour light (<10 lux)/12-hour dark cycle. At least 24 hours before experiments were initiated, mice were placed and maintained in a dark environment. Procedures were performed under dim red light transmitted through a safelight filter (transmittance >560 nm; No. 1; Kodak, Rochester, N.Y.). All animal procedures and experiments were approved by the Case Western Reserve University Animal Care Committee and conformed to recommendations of both the American Veterinary Medical Association Panel on Euthanasia and the ARVO Statement for the Use of Animals in Ophthalmic and Vision Research.

Retinoid Administration

All chitosan-retinoid compositions were administrated to Lrat−/− mice under dim red light. The chitosan-retinoid compositions were orally gavaged with soybean oil (95%, v/v) to a final concentration of 20 mg/mL. The soybean oil preparation (300 μL) was gavaged into mice as a single dose of 0.012 mg of retinoid/mouse.

Electroretinography (ERG) Recording $Lrat^{-/-}$ mice were dark-adapted prior to the procedure and then anesthetized by intraperitoneal injection of a mixture containing ketamine (80 mg/kg body weight) and xylazine (20 mg/kg body weight) in 10 mM sodium phosphate, pH 7.2, with 100 mM NaCl. Pupils were dilated with 1 drop of 1% tropicamide ophthalmic solution. ERG responses were measured with a universal testing and electrophysiologic system (UTAS with BigShot; LKC Technologies, Inc., Gaithersburg, Md.). To stabilize body temperature, mice were placed on a heated pad (37° C.) in a Ganzfeld chamber, where positioning of the contact lens electrodes was adjusted. Then two needle electrodes were placed under the skin of the forehead and tail as a reference and ground electrode, respectively, and two contact lens electrodes were placed on the eyes. Recording commenced when the lenses were well contacted and the baseline was stable. Single-flash ERGs were recorded simultaneously from both eyes with scotopic flash intensities (from −3.7 to 1.6 log cd sm$^{-2}$), and two to five recordings were made at sufficient intervals between flash stimuli (from 10-60 seconds) to allow mice time to recover. Amplitudes were measured by a commercial software package (EM software for Windows; LKC Technologies, Inc.) from baseline to the negative peak for a-waves and from the trough to the highest peak for b-waves.

Retinoid Analyses

All experimental procedures related to extraction, derivatization, and separation of retinoids were performed under dim red light provided by a Kodak No. 1 safelight filter (transmittance >560 nm). Retinoids were extracted twice with an equal volume of 100% hexane (6 mL total). The combined extracts were dried under argon, and retinoids were separated on a normal-phase HPLC column (Ultrasphere-Si, 5 μm, 4.6×250 mm; Beckman) with 10% ethyl acetate and 90% hexane at a flow rate of 1.4 mL/min and detected at 325 nm by an HPLC system (model HP1100; Hewlett Packard, with a diode array detector and HP Chemstation A.03.03 software).

Histologic Evaluation

Briefly, mouse eyecups were prepared immediately after euthanasia by removal of the cornea and lens. Eyecups were fixed in 2% glutaraldehyde, 4% paraformaldehyde and processed for embedding in Epon. Sections for routine histology were cut at 11 m and stained with toluidine blue.

HPLC Analysis of Eyes after Oral Gavage of Chitosan 9-Cis-Retinol Conjugate

To confirm whether orally gavaged chitosan 9-cis-retinol conjugates can produce 9-cis-retinal oximes in the eye, we extracted the retinoids from purified visual pigment of Lrat−/− mice orally gavaged chitosan 9-cis-retinol conjugates and detected 9-cis-retinal oximes. Significant amounts of 9-cis-retinal oximes were detected in eyes of treated mice exposed to intense light 6 hours after oral gavage and 23 hours after oral gavage (FIGS. 8A-B), whereas the amounts of 9-cis-retinal oximes were not detected in control groups not administered the therapeutic.

Improved ERG Responses in $Lrat^{-/-}$ Mice 1 Month after Oral Gavage of Chitosan 9-Cis-Retinol Conjugates Rod and cone functions of $Lrat^{-/-}$ mice become dramatically attenuated because of chromophore deficiency and resulting absence of visual pigments. Rods of $Lrat^{-/-}$ mice are approximately 2000-fold less sensitive to light stimuli than WT rods. Delivering the artificial 9-cis-retinoid chromophore to the retina leads to generation of the visual pigment, isorhodopsin, in Lratr mice, thereby restoring visual function. We recorded ERG responses in Lrat mice treated with chitosan 9-cis-retinol conjugates to monitor their visual function. All experiments were initiated with 5-week-old $Lrat^{-/-}$ mice. Chitosan 9-cis-retinol conjugates were orally administered to $Lrat^{-/-}$ mice in 6 oral gavages of 0.012 mg/mouse (n=9) over 2 weeks. All mice were maintained under a regular 12-hour light (<10 lux)/12-hour dark cycle. Three weeks after drug administration, mice were transferred to a darkroom for 1 week, and then single-flash scotopic ERGs were recorded. FIGS. 7 A-B show delivery of the oral gavage of chitosan 9-cis-retinol conjugates produced significant increases in both a-wave and b-wave amplitudes, starting at a stimulus intensity of 1.6 log cd·s·m$^{-2}$ for a-waves and 0.4 log cd·s·m$^{-2}$ for b-waves compared to baseline responses in untreated $Lrat^{-/-}$ mice. Thus, the increase of both ERG a-wave and b-wave amplitudes suggested that release of 9-cis-retinol from the chitosan 9-cis-retinol conjugates was sustained continuously as indicated in the retinoid-releasing profile. This maintained release of 9-cis-retinol caused an improvement of retinal function in $Lrat^{-/-}$ mice at even 4 weeks after administration, which was not attainable by single dose oral treatment.

Retinal Histology of 9-Cis-R-Ac-Treated $Lrat^{-/-}$ Mice

Figure 9A:
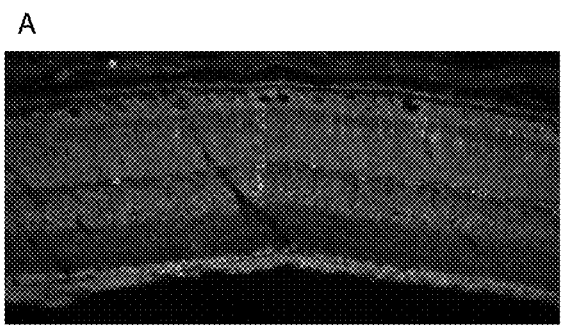
FIGS. 9(A-B) illustrate images showing the rod outer segment (ROS) layer of 5-week-old Lrat$^{-/-}$ mice administered a control or chitosan-9-cis-retinol conjugates.
Figure 9B:
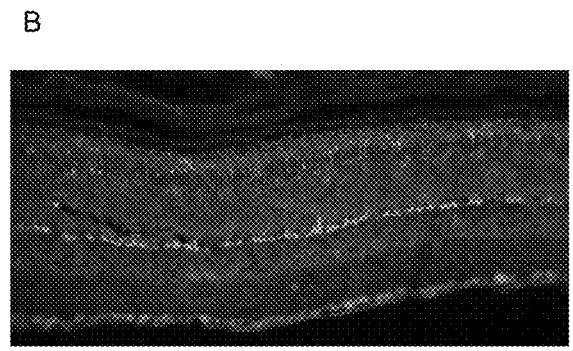

Functional rhodopsin (or isorhodopsin) is required to maintain normal ROS morphology. Therefore, if treatment of $Lrat^{-/-}$ mice with 9-cis-retinoids can restore visual function, it should also preserve ROS structure. Histologic analyses revealed that at the age of 6-8 weeks, ROS lengths of Lrat$^{-/-}$ mice were reduced to 65% of those observed in WT control mice. EM analysis of retinas demonstrated that ROS layers of Lrat$^{-/-}$ mice were shorter, thinner, and less tightly packed than those of WT mice. It was also reported that, after gavaging dark room reared Lrat$^{-/-}$ mice with a high dose of 9-cis-R-Ac (total dose of 72 mg in 6 gavages of 0.12 mg each over a two week duration), the ROS layer became substantially thicker, and the RPE-ROS interface displayed closer apposition than that seen in untreated control Lrat$^{-/-}$ mice. In this study, we observed histologic retention of ROS structures 1 month after oral gavage of chitosan 9-cis-retinol conjugates (FIGS. 9A-B). The ROS layer of the subcutaneous was thicker than that of the untreated control group, and more tightly packed than ROS layers untreated control groups.

From the above description of the invention, those skilled in the art will perceive improvements, changes and modifications Such improvements, changes and modifications are within the skill of the art and are intended to be covered by the appended claims. All publications, patents, and patent applications cited in the present application are herein incorporated by reference in their entirety.

Having described the invention, the following is claimed:

1. A method for treating a retinal disease in a subject, the method comprising:
   administering to the subject in need thereof a therapeutically effective amount of a composition, the composition consisting of a polysaccharide and at least one retinoid linked to at least one monosaccharide subunit of the polysaccharide via a hydrolysable carboxylic ester linkage, the linkage being degradable by hydrolysis during digestion of the composition to provide controlled, delayed, and/or sustained delivery of the at least one retinoid upon enteral administration of the composition to a subject, wherein the at least one retinoid comprises a retinal derivative.

2. The method of claim 1, wherein the at least one retinoid further linked to the at least one monosaccharide subunit of the polysaccharide via other linkages selected from the group consisting of ether, thioether disulfide, amide, imide secondary amine, direct carbon (C—C), sulfate ester, sulfonate ester, phosphate ester, urethane and carbonate hydrolysable covalent linkages.

3. The method of claim 1, wherein the at least one monosaccharide subunit of the polysaccharide having a carboxylate ion or amine residue, the carboxylate ion or amine residue being a component of the carboxylic ester linkage.

4. The method of claim 1, wherein the at least one retinoid is directly linked to the at least one monosaccharide subunit of the polysaccharide through a covalent linkage that comprises the carboxylic ester linkage.

5. The method of claim 1, wherein the carboxylic ester linkage is a component of a linker to connect the monosaccharide subunit of the polysaccharide to the retinoid, the linker having two or more functional groups that form hydrolysable covalent bonds to the at least one monomer subunit of the polysaccharide and to the retinoid.

6. The method of claim 1, wherein the monosaccharide subunit comprising at least one of β-D-mannuronate (M) or α-L-guluronate (G).

7. The method claim 1, wherein the polysaccharide comprising chitosan.

8. The method of claim 1, wherein the at least one retinoid comprising a synthetic retinoid of formula I, II, III, IV, V, VI, VII, VIII, IX, X, XI, XII, XIII, XIV, XV or XVI.

9. The method of claim 1, wherein the at least one retinoid comprising a retinol.

10. The method of claim 9, wherein the retinol is selected from the group consisting of 9-cis-retinol, 11-cis retinol, and combinations thereof.

11. A method for treating a retinal disease in a subject, the method comprising:
   administering to the subject in need thereof a therapeutically effective amount of a composition, the composition consisting of a polysaccharide and at least one 9-cis retinoid linked to at least one monosaccharide subunit of the polysaccharide via a hydrolysable carboxylic ester linkage, the linkage being degradable by hydrolysis during digestion of the composition to provide controlled, delayed, and/or sustained delivery of the at least one retinoid upon enteral administration of the composition to a subject.

12. The method of claim 11, wherein the monosaccharide subunit comprising at least one of β-D-mannuronate (M) or α-L-guluronate (G).

13. The method of claim 11, wherein the polysaccharide is chitosan.

14. The method of claim 11, wherein the 9-cis retinoid comprises 9-cis retinol.

* * * * *